United States Patent
Takamura et al.

(10) Patent No.: US 6,299,674 B1
(45) Date of Patent: Oct. 9, 2001

(54) FINGERPRINT DEVELOPING AGENT AND METHOD FOR DEVELOPING FINGERPRINTS

(75) Inventors: Yasuo Takamura, Mito; Masaharu Shimizu, Hitachinaka; Takashi Fukuchi; Fujio Ishizawa, both of Mito; Akira Miyagi, Fujisawa; Nobuyasu Ochiai, Yokohama; Atsushi Ikeda; Kiyoshi Okamura, both of Fujisawa, all of (JP)

(73) Assignee: Taiho Industries Co., Ltd. (JP)

( * ) Notice: Subject to any disclaimer, the term of this patent is extended or adjusted under 35 U.S.C. 154(b) by 0 days.

(21) Appl. No.: 09/440,034

(22) Filed: Nov. 12, 1999

(51) Int. Cl.$^7$ .................................................. C09D 11/00
(52) U.S. Cl. ................................. 106/31.14; 106/31.17; 106/31.32; 106/31.34; 106/31.64; 106/31.66
(58) Field of Search ............................. 106/31.14, 31.17, 106/31.32, 31.34, 31.58, 31.64, 31.66, 31.86

(56) References Cited

U.S. PATENT DOCUMENTS

| | | | |
|---|---|---|---|
| 4,182,261 | * | 1/1980 | Smith, III et al. ................. 118/31.5 |
| 4,879,134 | * | 11/1989 | Vassiliades ............................... 427/1 |
| 5,221,627 | | 6/1993 | Grigg et al. ............................. 436/89 |
| 5,919,292 | * | 7/1999 | Arndt ................................. 106/31.03 |
| 6,027,556 | * | 2/2000 | Arndt ................................. 106/31.35 |

FOREIGN PATENT DOCUMENTS

| | | |
|---|---|---|
| 57-11636A | 1/1982 | (JP) . |
| 61-58637A | 3/1986 | (JP) . |

\* cited by examiner

Primary Examiner—Helene Klemanski
Assistant Examiner—Veronica F. Faison
(74) Attorney, Agent, or Firm—Welsh & Katz, Ltd.; Thomas W. Tolpin

(57) ABSTRACT

A fingerprint detecting agent and a fingerprint detecting method using the agent, which can be used to detect latent fingerprints being in a wet condition, the fingerprint detecting agent includes a fixer containing silicone series compound, fluoride series compound, hydrocarbon series compound, animal or vegetable oil, higher fatty acid, or higher alcohol, and an arbitrary mixture thereof; a diluent containing polar soluent; a developer containing achromatic colored powder or chromatic colored powder. Latent fingerprints can be easily detected by spraying the fingerprint detecting agent; particularly, even if the latent fingerprints to be detected are in a wet condition, it is possible to detect them speedily and certainly.

21 Claims, 7 Drawing Sheets

FINGERPRINT DEVELOPING AGENT AND METHOD FOR DEVELOPING FINGERPRINTS

TECHNICAL FIELD

The present invention relates to a fingerprint detecting agent and a method for detecting fingerprints using the agent. More particularly, the present invention relates to a fingerprint detecting agent and a fingerprint detecting method by which latent fingerprints can be detected only by making the agent contact to the latent fingerprints. Particularly, according to the invention, even if latent fingerprints to be detected are in a wet condition, it is possible to detect them easily and speedily.

BACKGROUND ART

Fingerprints are an important proof aiding and arresting accused offenders and therefore to detecting fingerprints is a very important factor in criminal investigations. Conventional fingerprint detection is carried out in such a manner that aluminum powder is put on the surface of an object to be investigated where fingerprints adhere or on a surface of an object which is considered to have fingerprints adhered to there. The object is swept with a brush to adhere the powder on the latent fingerprints to actualize them; then the actualized fingerprint is printed on a gelatin paper (hereinafter called the "dry powder method").

However, in the conventional dry powder method, if the object to be investigated or the latent fingerprint adhered to on the object is wet, it is impossible to adhere the aluminum powder on to the latent fingerprint to actualize it; in such a case, it is necessary to wait until the object to be investigated, such as a wet window, a wet door, a wet of vehicle body or any other article left on a criminal site, gets dry or to make them dry by using, for example, a dryer. Such processes are complicated, and further the latent fingerprints sometimes disappear in such wet conditions. In this manner, according to the conventional dry powder method, it is very difficult to detect fingerprints, particularly, outside under wet rainy weather.

On the other hand, the conventional dry powder method requires a skill to actualize the latent fingerprint by swiping. Therefore, a non-skilled person sometimes causes damage to the ridged line of the fingerprint to be detected in spite of the wet or dry conditions.

Further, in case the surface of the object to be investigated is large or a large number of the articles are left at a criminal site, the wiping work is so hard because the operator has to wipe them with a brush continuously and very carefully at every small region, for example, 10×10 cm square or on every article left at the site.

DISCLOSURE OF INVENTION

The present invention has for its object to provide a fingerprint detecting agent and a method for detecting fingerprints using the agent by which latent fingerprints can easily be detected by only spraying the agent, particularly, even if the latent fingerprints are in a wet condition, it is possible to detect them speedily and certainly.

In order to carry out the above object, the present inventors created a way to cover the latent fingerprints with the agent and simultaneously to remove the water which adheres on the latent fingerprints and then actualize the fingerprint with the cover by spraying a powder. The present inventors found out that if an agent containing a mixture of a special kind of fixer and developer is applied to actualize the latent fingerprint, the above object can be achieved.

That is to say, the fingerprint detecting agent according to the present invention, can be used to detect latent fingerprints in a wet condition; contains a fixer, a diluent, and a developer; said fixer contains at least one selected from a group consisting of a silicone series compound, a fluorine series compound, hydrocarbon series compound, animal and/or vegetable oil, a higher fatty acid and a higher alcohol; said diluent contains a polar solvent; and said developer contains achromatic or chromatic powder.

Further, the method for detecting fingerprints according to the present invention using said fingerprint detecting agent has a feature that the fingerprint detecting agent is made to contact to a latent fingerprint to be detected.

The detail is still not apparent as to why latent fingerprints, particularly, latent fingerprints in a wet condition can be detected so quickly, but it may be guessed as in the following.

That is to say, when the diluent is mixed with the oil component contained in the fingerprint to be detected, the latent fingerprint is made to contact the developer to cause an absorption reaction so that the fingerprint is actualized; at the same time, the whole surface of the object to be investigated where the developer adheres is coated with the fixer. Then, the developer adhering to the other portion of the fingerprint is removed in a washing process with a water because the adhering force between the developer and the other portion is weak, so that only the developer adsorbed by the fingerprint portion remains.

The fingerprint detecting agent according to the present invention will be explained in detail.

As stated above, the fingerprint detecting agent according to the invention contains a fixer, a diluent and a developer.

Silicone series compound, fluoride series compound, hydrocarbon series compound, animal oil, vegetable oil, higher fatty acid, and higher alcohol and an arbitrary mixture of these materials can be cited as the fixer.

Further, denaturing silicone and/or dimethyl silicone can be cited as the silicone series compound; an amino denaturing silicone, alkyl denaturing silicone, carboxy denaturing silicone, polyalkylen denaturing silicone or epoxy denaturing silicone and an arbitrary mixture of these materials can be stated as the denaturing silicone.

Furthermore, it is preferred to use a silicone series compound having a boiling point more than 250° C., because the compound having a boiling point less than 250° C. sometimes volatizes.

When the dimethyl silicone is used, it is preferred to use a dimethyl silicone having a viscosity of about 2~1000 cSt. If the viscosity of the dimethyl silicone is smaller than 2 cts, the silicone is volatized so that the fixing force thereof is significantly decreased. On the other hand, when the viscosity exceeds over 1000 cSt, the stabilization for storing the fingerprint detecting agent decreases.

A fluoride oil, and fluoride resin dispersion can be cited as the fluoride compound, but a fluoride oil is preferred. Such a fluoride oil is represented by the following chemical formulae (1) and (2).

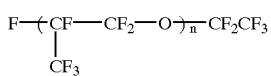
(1)

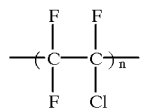
(2)

Next, the diluent should contain a polar solvent, but it is not limited if the fixer and the solute can be dispersed uniformly by the diluent.

For the polar solvent, water, any kind of alcohol or a mixture thereof can be cited as an example; a lower alcohol having a carbon number of 1 to 3 can be stated as an example of the alcohol, particularly, isopropylalcohol can be preferably used.

The other usable solvents are: alcohol having one valency, alcohol having a plurality of valencies, glycol ether, acetate, alkanolamine, ketone group and ether group. Further, it may be possible to add a stabilizer assistant into the agent in order to improve the stabilization of the solvent in the liquid phase of the agent. As such a stabilizer assistant, an organic acid, such as carboxylic acid and sulfonic acid; a non organic acid, such as hydrochloric acid, sulfuric acid and nitric acid; a non-organic alkali, such as ammonia and sodium hydroxide; an organic amine, such as morpholine; a surface active agent, etc. can be stated.

In case that the mixture of amino denaturing silicone and dimethyl silicone is used as the fixer, it is preferred to use a mixed liquid of water and isopropyl alcohol as a diluent. Further, an organic acid, such as carboxylic acid, sulfonic acid and sulfinic acid; a non-organic acid, such as hydrochloric acid, sulfuric acid, and nitric acid; and surface active agent, etc. can be preferably used as a stabilization assistant at this stage. Furthermore, a preservative, such as parabens, etc. may be added.

As non-colored or colored powder contained in the developer, several kinds of non-organic or organic powder can be used. For instance, barium sulfate, calcium carbonate, gypsum, alumina, agalmatolite, lithopone, zinc oxide, silicon oxide or titanium oxide, and an arbitrary mixture of these materials can be stated as a white series non-colored powder. While, carbon black, graphite, molybdenum disulfide, iron oxide, silica black, chrome black, mineral black, vine black, bone black or silicon carbonate and an arbitrary mixture of these materials can be cited for the black series non-colored powder.

Further, a red pigment, such as red oxide, red lead, cadmium red, molybdenum red, copper ferrocyanide; yellow pigment, such as chrome yellow, yellow oxide, yellow ochre, barium yellow and cadmium yellow; a green pigment, such as chrome green, cobalt green, manganese green, iron green phosphonic acid copper and verdigris, etc; a blue pigment, such as Milori blue, ultramarine blue, cobalt blue and tungsten blue; metal powder, such as aluminum powder, bronze (copper-zinc alloy) powder; or an organic pigment can be stated. These powder can be used individually or in a mixed manner.

It should be noted that it is preferred that such powder has a particle diameter of 75 $\mu$m or less, more preferably 10~60 $\mu$m, the most preferably 20~30 $\mu$m in order to disperse the particles into a liquid phase of the agent and to improve the adhering characteristic thereof to the latent fingerprint. If the particle diameter of the powder exceeds over 75 $\mu$m, the flowing speed of the agent containing the powders when the agent is sprayed on the latent fingerprint becomes too fast, so that the contacting time of the liquid phase of the agent and the latent fingerprint becomes short and then the amount of the agent which adheres to the fingerprint becomes small; while, if the particle diameter is 10 $\mu$m or less, it becomes difficult to manufacture the powder and the cost for manufacturing becomes high.

In case that the base surface of the object to be investigated on which latent fingerprints are added is black or dark colored, white or the other bright colored powder should be added and dispersed to the fingerprint detecting agent in order to accelerate the actualization of the latent fingerprint. In this case, a mixture of agalmatolite, lithopone, and zinc oxide is preferably used as the white powder.

On the other hand, if the base surface of the object is white or bright colored, black or dark colored powder should be added and dispersed to the agent. In this case, a mixture of carbon black and graphite can be preferably used.

It should be noted that gold colored powder more concretely, bronze powder or copper powder can be used for both the black or dark colored object and the white or bright colored object.

The mixing amount of the above-mentioned compositions will be explained. The mixing ratio of the compositions contained in the fingerprint detecting agent according to the invention should be decided so as to assure the actualization of the latent fingerprint by making the agent contact to the latent fingerprint. The typical mixing ratio is: 0.1~5.0 part by weight of silicone series compound, 85.0~98.9 part by weight of diluent and 1.0~10.0 part by weight of non-colored or colored powder.

In the above-mentioned mixing ratio, when the ratio of the silicone series fixer is only 0.1 part by weight or less, it becomes difficult to form a fixing film, however, if it exceeds over 5.0 parts by weight, the thickness of the fixing film becomes so thick that the fingerprint cannot be detected.

In addition to this, if only 85.0 parts by weight or less of diluent is contained, the fixing composition will be deposited in the agent so that a fixing film having a uniform thickness cannot be obtained; while if the ratio of the diluent is 98.8 parts by weight or more, the amount of the fixing composition becomes small and thus a film having a uniform thickness cannot be formed either.

Further, when the developer contained in the agent is 1.0 part by weight or less, the fingerprint cannot be actualized clearly, but the ratio of the developer exceeds over 10 part by weight, the developer will adhere to some other region than the fingerprint so that it becomes difficult to detect the fingerprint clearly.

In case that a mixed liquid of water and a lower alcohol is used as the diluent, it is preferred to mix 50.0~95.0 parts by weight of water and 0~50.5 parts by weight of isopropyl alcohol.

If the composition amount of the water exceeds the above stated range, the stabilization of the agent becomes insufficient so that a fixing film having a uniform thickness cannot be obtained.

While, if the composition amount of the lower alcohol exceeds the above range, the stabilization of the liquid also becomes insufficient so that a fixing film having a uniform thickness cannot be obtained.

It should be noted that 0.01~0.5 parts by weight of organic acid can be preferably added to the agent as a stabilizer, but if the composition amount of the stabilizer exceeds this range, the stabilization of the agent becomes insufficient.

Further, when the mixture of agalmatolite, lithopone and zinc oxide is used as the white powder, it is preferred to take a mixture ratio of 75~85 parts by weight of agalmatolite, 5~15 parts by weight of lithopone and 5~15 parts by weight of zinc oxide.

On the other hand, when the mixture of carbon black and graphite is used as the black powder, it is preferred to take a mixture ratio of 40~50 parts by weight of carbon black and 50~60 parts by weight of graphite. However, the other mixture ratio can be applied to control the amount of the powder to be added to the fingerprints for actualizing the latent fingerprints.

Since the fingerprint detecting agent according to the present invention contains every kind of powder as a developer, there is still some possibility left that the sedimentation stabilization of the developer becomes insufficient over a long time period, or that the rest portion of the object where fingerprints are detected do not adhere and becomes contamined with the powder when the fingerprints are detected.

In such a case, the liquid phase content of the agent including the fixer and the diluent may be preserved separately from the developer in order to avoid the problem that the sedimentation stabilization for a long time period becomes worse; the liquid phase content and the developer may be mixed together to obtain a suitable fingerprint detecting agent as occasion demands, at, for example, the investigating site. The thus mixed agent can be used to actualize fingerprints by being applied or sprayed on to the fingerprints. The agent can be also used in such a manner that the liquid phase content is preliminarily sprayed on the portion where fingerprints adhered and then the powder is applied thereon so that the latent fingerprints are actualized by using a normal powder technique.

The fingerprint detecting method according to the invention will be explained below.

As stated above, the method for detecting fingerprints according to the invention is to make the fingerprint detecting agent explained above contact to latent fingerprints; it is preferred that the agent is washed out to remove the excess powder after making contact.

It is preferred to carry out contact by spraying the agent to latent fingerprint or immersing the object to be detected into the agent. When latent fingerprints, which adhered to a wall surface, for instance, on an investigating site will be detected, it may spray the agent on the whole surface of the wall. While, in case there are many articles left such as a plurality of cans on the spot, it may be possible to immerse all or some of the cans in the agent to detect fingerprints.

How to spray the agent or how to immerse the articles in the agent is not limited. For instance, manual or automatic type pumping containers, in which the agent is filled, may suitably be used to spray; and also other styles, for example, aerosol style may be also applied to spray the agent. It should be noted that the washing process mentioned above can be conducted only by putting some water on the actualized fingerprints.

According to the method for detecting fingerprints of the present invention, the latent fingerprints can be detected by an easy way, such as spraying or immersing. Therefore, the fingerprints can be detected more speedily and easily without any special technique in comparison to conventional powder techniques.

Particularly, even if latent fingerprints are wet, it is possible to spray the agent on the object or immerse the objects into the agent instantly without making the object dry, which is a different point from the conventional powder techniques. Therefore, it is possible to make the detection time shorter which is necessary to detect fingerprints.

The fingerprints actualized by spraying the agent on the object or immersing the objects in the agent can be preserved by printing the actualized fingerprint on, for instance, gelatin paper the same as the conventional technique.

The materials for the object to be detected, to which the fingerprint detecting agent according to the invention can be suitably applied, are any article other than paper and craft tape with gum, i.e. any sort of metal, plastic, ceramics; more concretely, glass, vehicle body, bottle, can, window frame made of aluminum, new construction materials made of woods, safety cone, etc. As stated above, the fingerprints can be clearly actualized even if the materials are wet.

However, if a considerable amount of oil adheres on the object to be detected, the detection of the fingerprints sometimes becomes difficult, because an oil composition of the fingerprints is solved into the oil adhered on the object. In this meaning, a pistol which is mostly maintained with lubricating oil or rust proof oil is one of the objects which are difficult to conduct the detection of the fingerprints by using the agent of the present invention.

BEST MODE FOR CARRYING OUT THE INVENTION

The present invention will be explained below more detail, referring some preferred embodiments, but the scope of the claims is not limited to the following embodiments.

(Embodyment 1)

Amino denaturing silicone of 1.0 part by weight, demethirsilicone of 1.0 part by weight (having a 20 cP of viscosity), isopropyl alcohol of 20 parts by weight, acetic acid of 0.1 part by weight, butyl parabens of 0.1 part by weight as a preservative and ion exchange water of 77.8 parts by weight were mixed and stirred up together.

To the thus obtained mixed solvent of 100 parts by weight, was added and mixed a developer, i.e. white powder (agalmatolite of 80 weight percents, lithopon of 10 weight percents, and zinc oxide of 10 weight percents) having its particle diameter of 30~54 μm or black powder (carbon black of 45 weight percents and graphite of 55 weight percents) having its particle diameter of 20~50 μm, at a rate shown in the Table 1 to obtain fingerprint detecting agents.

The thus obtained fingerprint detecting agents were tested in accordance with the below mentioned method; the result thereof is shown in the Table 1.

(Fingerprint Detecting Test)

A piece of glass, a vehicle body, and an Aluminum window frame (silver colored) were used as objects to be detected, each of which becomes an object for detecting fingerprints on actual sites of criminal with a high frequency. After adhering a fingerprint on each object, water was sprayed on the objects to make the lateral fingerprints wet. Then each of the fingerprint detecting agents mentioned above was sprayed on each of the thus prepared object; after 10 to 30 seconds, water was put again to remove the excessive powder.

The thus actualized fingerprints were judged with naked eyes; the result of the judgement is shown in Table 1.

Figure 1:
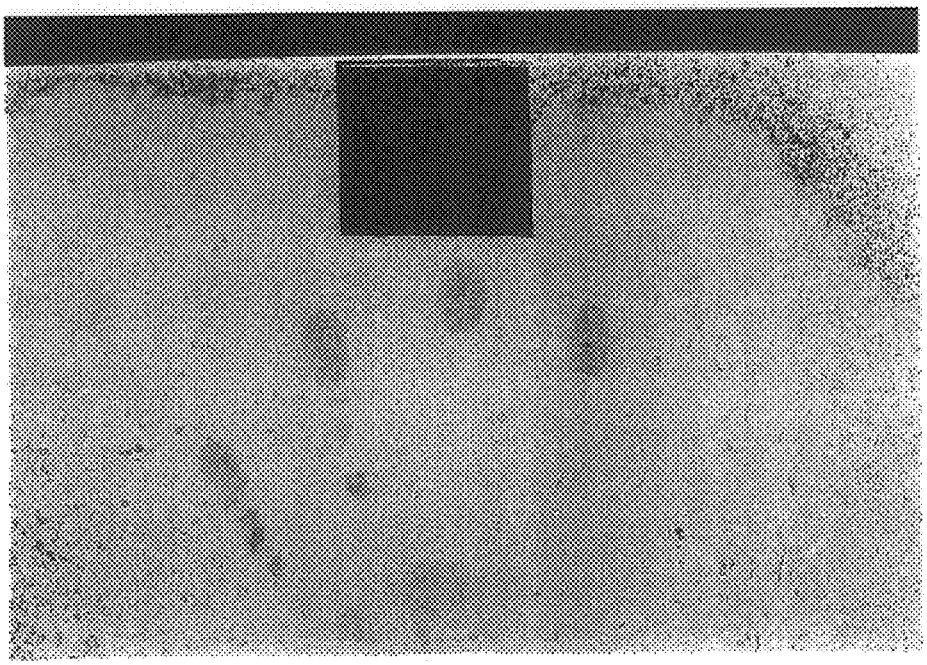
FIG. 1 is a photograph showing the result of a fingerprint detecting experiment.
Figure 2:
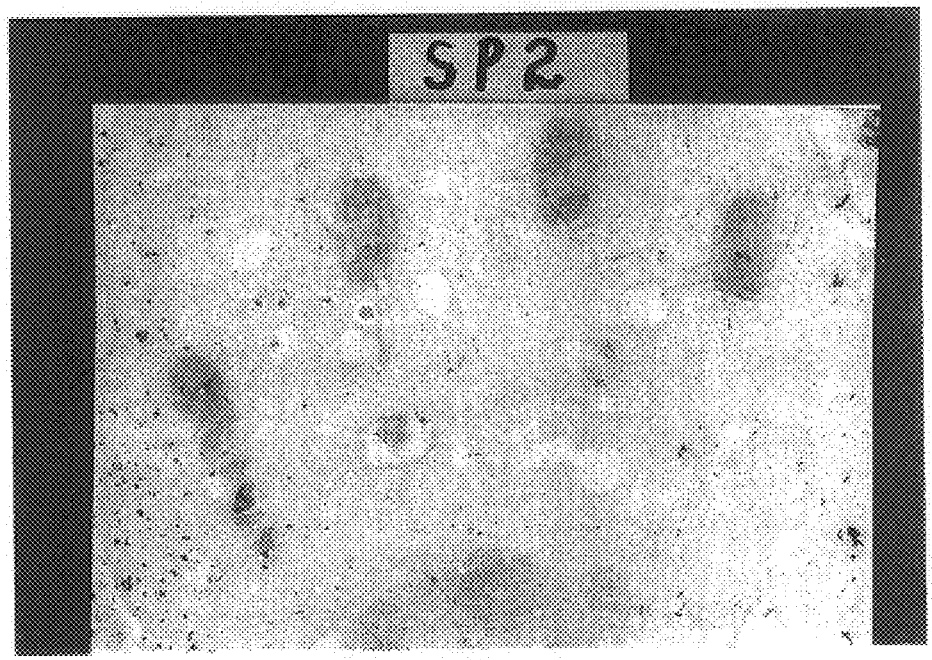
FIG. 2 is a photograph representing the print on gelatin paper for the fingerprint shown in FIG. 1.

FIG. 1 is a photograph showing the result of the experiment where the fingerprint detecting agent, to which 5 g of black powder was added, was used to detect a fingerprint which adhered to a vehicle body; and FIG. 2 is a photograph of the thus obtained fingerprint which was printed on a gelatin paper.

(Embodiment 2)

The same operation as that of the Embodiment 1 was taken excepting for that Aluminum powder (having a particle diameter of about 50 μm), SP powder (a mixture of hydrated aluminum, iron oxide and aluminum which has a particle diameter of about 50 μm) or yellow powder (a mixture of yellow pigment and lycopodium spores which has a particle diameter of about 50 μm ) was used instead of the white powder or black powder. The experimental result is shown in Table 1.

TABLE 1

| | Powder | Added Amount | Glass | Vehicle Body | Aluminum Frame |
|---|---|---|---|---|---|
| Embodiment 1 | Black Powder | 2.0 | Δ | Δ | Δ |
| | | 3.0 | ○ | ○ | ○ |
| | | 4.0 | ◎ | ◎ | ◎ |
| | | 5.0 | ◎ | ◎ | ◎ |
| | | 6.0 | ◎ | ◎ | ◎ |
| | | 7.0 | ○ | ○ | ○ |
| | White Powder | 2.0 | Δ | Δ | Δ |
| | | 3.0 | ○ | ○ | ○ |
| | | 4.0 | ◎ | ◎ | ◎ |
| | | 5.0 | ◎ | ◎ | ◎ |
| | | 6.0 | ◎ | ◎ | ◎ |
| | | 7.0 | ○ | ○ | ○ |
| Embodiment 2 | Aluminum Powder | 2.0~7.0 | Δ | Δ | Δ |
| | SP black Powder | 2.0~7.0 | Δ | Δ | Δ |
| | Yellow Powder | 2.0~7.0 | Δ | Δ | Δ |

* The added amount is represented by part by weight
◎: extremely clear

TABLE 1-continued

| Powder | Added Amount | Glass | Vehicle Body | Aluminum Frame |
|---|---|---|---|---|

○: clear
Δ: a little unclear

From Table 1, it is proved that the fingerprints can be detected in a good manner according to the embodiments 1 and 2. Since the thus actualized fingerprints are coated with the agent, it is possible to print the fingerprints on gelatin paper while the fingerprints being kept in a wet condition. However, better results could be obtained by absorbing some water content therefrom using a piece of kitchen paper before printing the fingerprint on the gelatin paper. It is also fine to print the fingerprints on the gelatin paper after making them dry by using a dryer.

As clear from the above, it is possible to detect clear fingerprints easily and speedily by using fingerprint detecting agent according to the invention even if the fingerprints are left outside under a rainy weather.

(Embodiments 3 to 8)

The same fingerprint detecting operation as that of the Embodiment 1 were repeated but with different mixing ratios of the compositions of the fingerprint detecting agent as shown in Table 2, obtained several sorts of fingerprint detecting agents. The above-mentioned fingerprint detecting experiments were conducted using the thus obtained fingerprint detecting agents. The result of the experiments is mentioned on Table 2.

Figure 3:
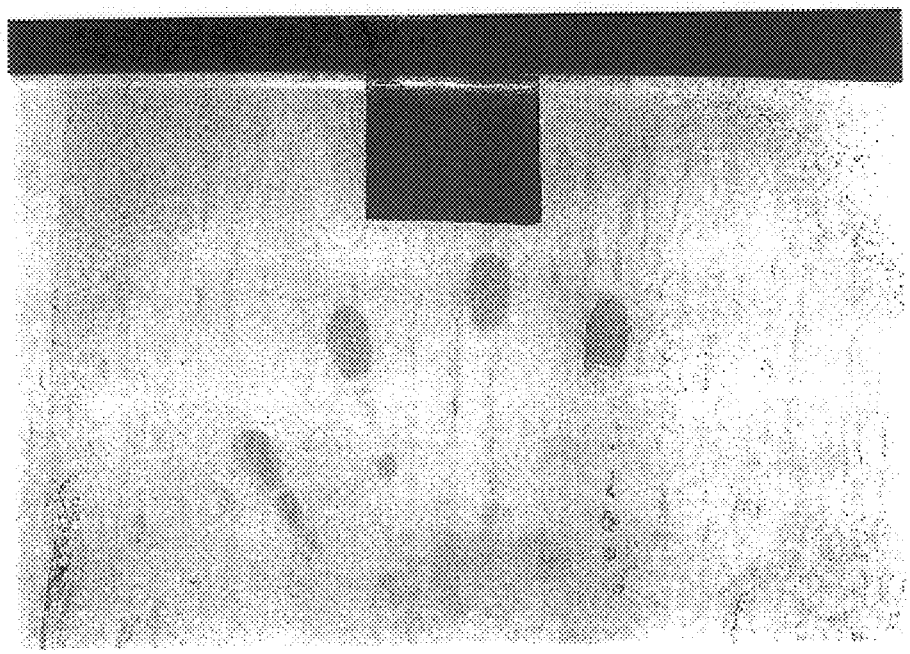
FIG. 3 is a photograph depicting the result of a fingerprint detecting experiment.
Figure 4:
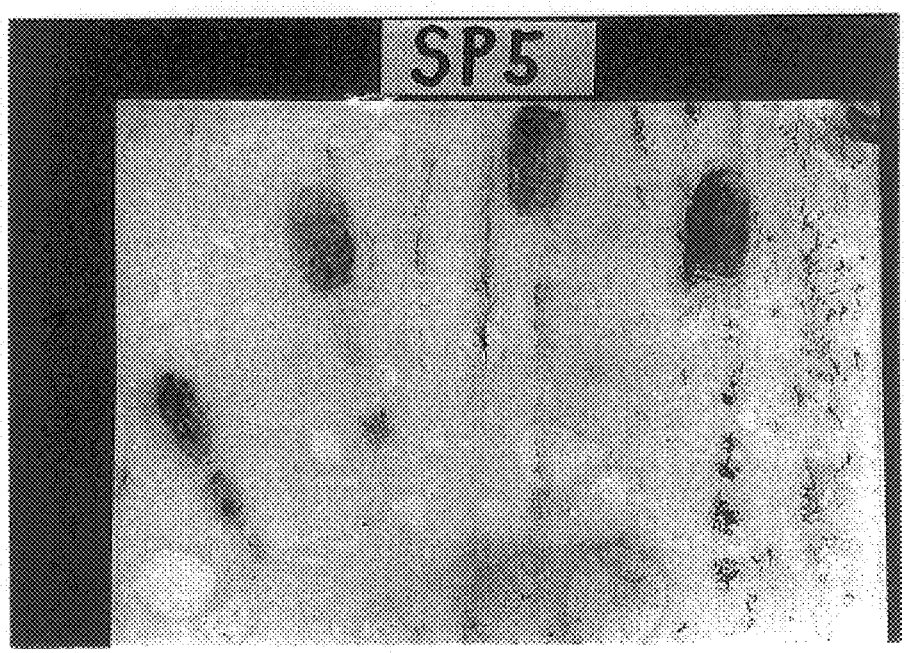
FIG. 4 is a photograph representing the print on gelatin paper for the fingerprint shown in FIG. 3.

FIG. 3 shows a result of an experiment where a fingerprint adhered on a vehicle body is detected by using the fingerprint detecting agent according to the Embodiment 7; and the printed result of the thus obtained fingerprint is shown in FIG. 4.

TABLE 2

| Embodiment | 3 | 4 | 5 | 6 | 7 | 8 |
|---|---|---|---|---|---|---|
| Dimethyl Silicone | | | | | | |
| 5 cp | — | 1.5 | — | — | — | — |
| 20 cp | 0.5 | — | — | — | — | 1.0 |
| 50 cp | — | — | — | 1.0 | — | — |
| 100 cp | — | — | 0.5 | — | — | — |
| 800 cp | — | — | — | 0.3 | — | — |
| Amino Denaturing Silicone | 1.5 | 1.0 | 1.5 | 1.5 | 1.0 | 1.0 |
| Isopropyl Alcohol | 10.0 | 20.0 | — | 30.0 | 15.0 | 10.0 |
| Normal-propyl Alcohol | 10.0 | — | 25.0 | — | — | — |
| Acetic Acid | — | 0.1 | 0.1 | — | 0.1 | — |
| Preservative | 0.2 | 0.2 | — | — | 0.2 | 0.2 |
| Perfume | 0.2 | — | 0.2 | 0.2 | — | 0.2 |
| Ion Exchange Water | 77.6 | 77.2 | 72.3 | 68.0 | 82.7 | 87.6 |
| Black Powder | 5 | 5 | 5 | 5 | 5 | 5 |
| Result | | | | | | |
| Glass | ◎ | ◎ | ◎ | ○ | ◎ | ○ |
| White Colored Vehicle Body | ◎ | ◎ | ◎ | ○ | ◎ | ○ |
| Aluminum Flame | ◎ | ◎ | ◎ | ○ | ◎ | ○ |

* The added amount is represented by part by weight
◎: extremely clear
○: clear
Δ: a little unclear

COMPARATIVE EXAMPLE 1

SUMIKAGEL™ (Acquakeep 10SH-P, a name of products manufactured by Sumitomo Fine Chemical Co., Ltd.) and aluminum powder were mixed together at a weight ratio of 6.5:1 to obtain a fingerprint detecting powder; a fingerprint detecting experiment was conducted for a fingerprint adhered on a vehicle body. As a result, the water content adhered on the object, i.e. the vehicle body, was absorbed by the SUMIKAGEL™ so that some grains of the SUMIKAGEL™ were generated. The objected fingerprint was actualized by aluminum powder, however, the fingerprint should be wiped by a brush after the actualization, and thus there was a fear that the ridged line of the fingerprint was damaged by the grains of the SUMIKAGEL™.

Further, the fingerprint detecting operations were not easy outside under a rainy weather.

COMPARATIVE EXAMPLE 2

Titanium dioxide and iron oxide were processed to obtain super fine particles thereof having a particle diameter of 0.03 to 0.05 µm and then Fluoride process was given to them to obtain different types of fingerprint detecting powder. The same operations as that of the comparative example 1 were repeated for detecting a fingerprint. As a result, there was still left a fear that the ridged line of the fingerprint was damaged by brushing operation.

(Embodiment 9)

Amino denaturing silicone of 1.0 part by weight, dimethyl silicone oil (20 cP of viscosity) of 1.0 part by weight, isopropyl alcohol of 20.0 part by weight, aceto acid of 0.1 part by weight, butyl parabens of 0.1 weight part as a preservative, and ion exchange water of 77.8 parts by weight were mixed and stirred together to obtain a mixture solvent. Zinc oxide of 5 parts by weight was added to the thus obtained mixture of 100 parts by weight as a developer to obtain a fingerprint detecting agent according to the invention.

A fingerprint detecting test was held in the same manner to the first embodiment but using the fingerprint detecting agent obtained in the above mentioned manner was used. The result is shown in Table 3. Further, the stabilization of the solvent of the fingerprint detecting agent was evaluated by a sedimentation speed and a re-dispersing characteristic; the result is also shown in Table 3. It should be noted that the mark ⊚ means "very good" and the mark ○ means "good" for the evaluation of the stabilization of the solvent.

(Embodiment 10)

The same operations as those in the Embodiment 9 were taken to obtain a fingerprint detecting agent except that carbon black was used as a developer instead of the zinc oxide. The obtained result is shown in Table 3.

(Embodiment 11)

The same operations as those in the Embodiment 9 were taken to obtain a fingerprint detecting agent except that white powder, which is used in the embodiment 1, was used as a developer instead of the zinc oxide. The obtained result is shown in Table 3.

(Embodiment 12)

The same operations as those in the Embodiment 9 were taken to obtain a fingerprint detecting agent except that black powder, which is used in the embodiment 1, was used as a developer instead of the zinc oxide. The obtained result is shown in Table 3.

(Embodiment 13)

The same operations as those in the Embodiment 9 were taken to obtain a fingerprint detecting agent except that 2.0 part by weight of ethylene chloride trifluoride oil was used instead of the amino denaturing silicone and the demethyle silicone. The obtained result is shown in Table 3.

(Embodiment 14)

The same operations as those in the Embodiment 13 were taken to obtain a fingerprint detecting agent except that white powder, which is used in the embodiment 1, was used as a developer instead of the zinc oxide. The obtained result is shown in Table 3.

(Embodiment 15)

The same operations as those in the Embodiment 13 were taken to obtain a fingerprint detecting agent except that black powder, which is used in the embodiment 1, was used as a developer instead of the zinc oxide. The obtained result is shown in Table 3.

(Embodiment 16)

The same operations as those in the Embodiment 11 were taken to obtain a fingerprint detecting agent except that 2.0 parts by weight of liquid paraffin (the name of product "MORESCOWHIITE P-70™: a name of product manufactured by Matsumura Oil Laboratory) was used instead of the amino denaturing silicone and the demethyle silicone. The obtained result is shown in Table 3.

(Embodiment 17)

The same operations as those in the Embodiment 11 were taken to obtain a fingerprint detecting agent except that 2.0 parts by weight of oleic acid was used instead of the amino denaturing silicone and the demethyle silicone. The obtained result is shown in Table 3.

(Embodiment 18)

The same operations as those in the Embodiment 12 were taken to obtain a fingerprint detecting agent except that 2.0 parts by weight of higher alcohol (DOBANOL23™: a name of product manufactured by Mitsubishi Oil Chemical Co., Ltd.) was used instead of the amino denaturing silicone and the demethyle silicone. The obtained result is shown in Table 3.

(Embodiment 19)

The same operations as those in the Embodiment 12 were taken to obtain a fingerprint detecting agent except that 2.0 part by weight of alkyl denaturing silicone was used instead of the amino denaturing silicone and the demethyle silicone. The obtained result is shown in Table 3.

(Embodiment 20)

The same operations as those in the Embodiment 12 were taken to obtain a fingerprint detecting agent except that the same amount of methanol was used instead of isopropyl alcohol of the diluent consisting of 20 parts by weight of isopropyl alcohol, 0.1 weight part of acetic acid, 0.1 weight part of butyl parabens as a preservative and 77.8 parts by weight of ion exchange water. The obtained results is shown in Table 3.

(Embodiment 21)

The same operations as those in the Embodiment 20 were taken to obtain a fingerprint detecting agent except that ethanol was used instead of methanol. The obtained result is shown in Table 3.

(Embodiment 22)

The same operations as those in the Embodiment 20 were taken to obtain a fingerprint detecting agent except that n-propyl alcohol was used instead of methanol. The obtained result is shown in Table 3.

(Embodiment 23)

The same operations as those in the Embodiment 9 were taken to obtain a fingerprint detecting agent except that aluminum powder was used instead of zinc oxide. The obtained result is shown in Table 3.

(Embodiment 24)

The same operations as those in the Embodiment 9 were taken to obtain a fingerprint detecting agent except that ultramarine blue was used instead of zinc oxide. The obtained result is shown in Table 3.

(Embodiment 25)

The same operations as those in the Embodiment 12 were taken to obtain a fingerprint detecting agent except that 2.0 parts by weight of epoxy denatured silicone was used instead of the amino denaturing silicone and the demethyle silicone. The obtained result is shown in Table 3.

(Embodiment 26)

The same operations as those in the Embodiment 11 were taken to obtain a fingerprint detecting agent except that 2.0 part by weight of fluorine series resin (Lumifron LF60: a name of product manufactured by Asahi Glass Co., Ltd.) was used instead of the amino denaturing silicone and the demethyle silicone. The obtained result is shown in Table 3.

(Embodiment 27)

The same operations as those in the Embodiment 9 were taken to obtain a fingerprint detecting agent except that blood red was used instead of the zinc oxide. The obtained result is shown in Table 3.

(Embodiment 28)

The same operations as those in the Embodiment 12 were taken to obtain a fingerprint detecting agent except that 2.0 parts by weight of alkyl denaturing silicone oil was used instead of the amino denaturing silicone and the dimethyl silicone. The obtained result is shown in Table 3.

TABLE 3

| Embodiment | Stabilization of the Soluent (Color of Powder) | Glass | Vehicle Body White | Vehicle Body Black | Aluminum Flame |
|---|---|---|---|---|---|
| 9  | ◎ (White) | ○ | Δ | ○ | ○ |
| 10 | ◎ (Black) | ○ | ◎ | Δ | ○ |
| 11 | ◎ (White) | ◎ | Δ | ○ | ◎ |
| 12 | ◎ (Black) | ◎ | ◎ | Δ | ◎ |
| 13 | ◎ (White) | ○ | Δ | ◎ | ○ |
| 14 | ◎ (White) | ◎ | Δ | ○ | ○ |
| 15 | ◎ (Black) | ◎ | ◎ | Δ | ◎ |
| 16 | ◎ (White) | ◎ | Δ | ◎ | ○ |
| 17 | ◎ (White) | ○ | Δ | ◎ | ○ |
| 18 | ◎ (Black) | ○ | ◎ | Δ | ○ |
| 19 | ◎ (Black) | ◎ | ◎ | Δ | ◎ |
| 20 | ◎ (Black) | ○ | ○ | Δ | ○ |
| 21 | ◎ (Black) | ○ | ○ | Δ | ○ |
| 22 | ◎ (Black) | ◎ | ◎ | Δ | ◎ |
| 23 | ○ (White) | ◎ | Δ | ◎ | Δ |
| 24 | ◎ (Blue) | ◎ | ◎ | Δ | ◎ |
| 25 | ○ (Black) | ◎ | ◎ | Δ | ◎ |
| 26 | ○ (White) | ◎ | Δ | ◎ | ◎ |
| 27 | ○ (Red) | ◎ | ◎ | Δ | ○ |
| 28 | ◎ (Black) | ◎ | ◎ | Δ | ◎ |

◎: extremely clear
○: clear
Δ: a little unclear (Embodiment 29)

Into 100 parts by weight of mixed solvent obtained in the embodiment 1, added 5 parts by weight of the above-said white powder or black powder to obtain a different type of fingerprint detecting agent.

The thus obtained agent was sprayed on each specimen which was kept dry and on which a fingerprint was adhered; then the excess powder was washed out; the experimental result is shown in Table 4 and FIGS. 5 to 14.

Figure 5:
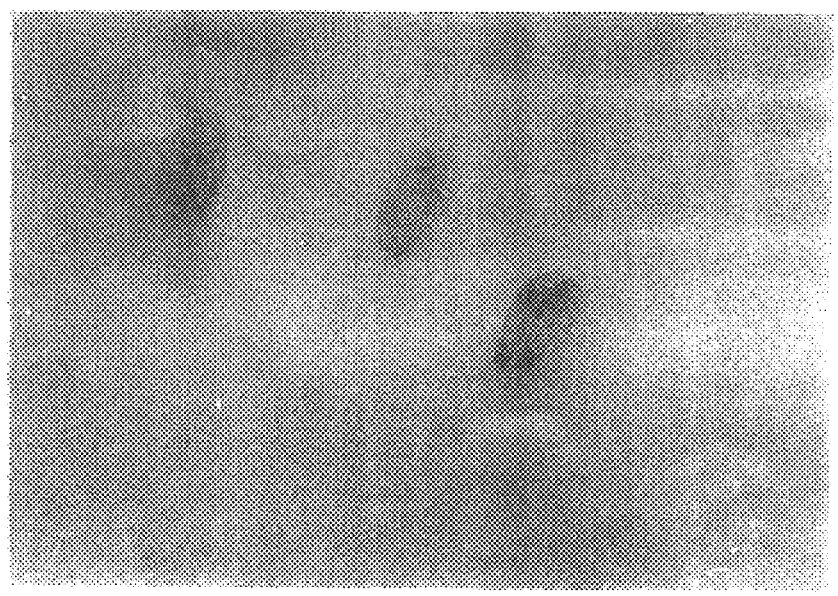
FIG. 5 is a photograph depicting the result of a fingerprint detecting experiment.
Figure 6:
FIG. 6 is a photograph representing the print on gelatin paper for the fingerprint shown in FIG. 5.
Figure 7:
FIG. 7 is a photograph depicting the result of a fingerprint detecting experiment.
Figure 8:
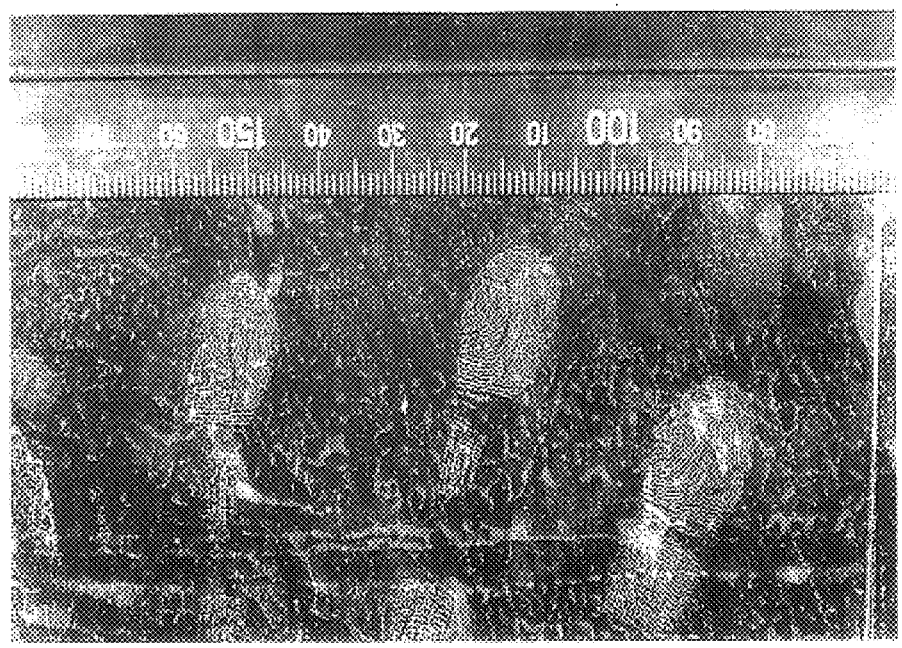
FIG. 8 is a photograph representing the print on gelatin paper for the fingerprint shown in FIG. 7.
Figure 9:
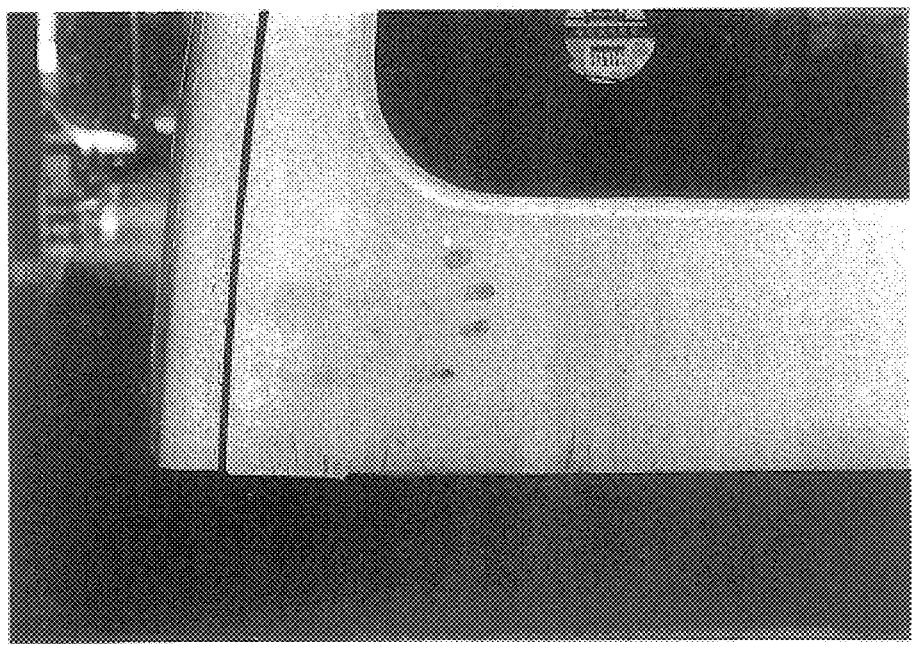
FIG. 9 is a photograph depicting the result of a fingerprint detecting experiment.
Figure 10:
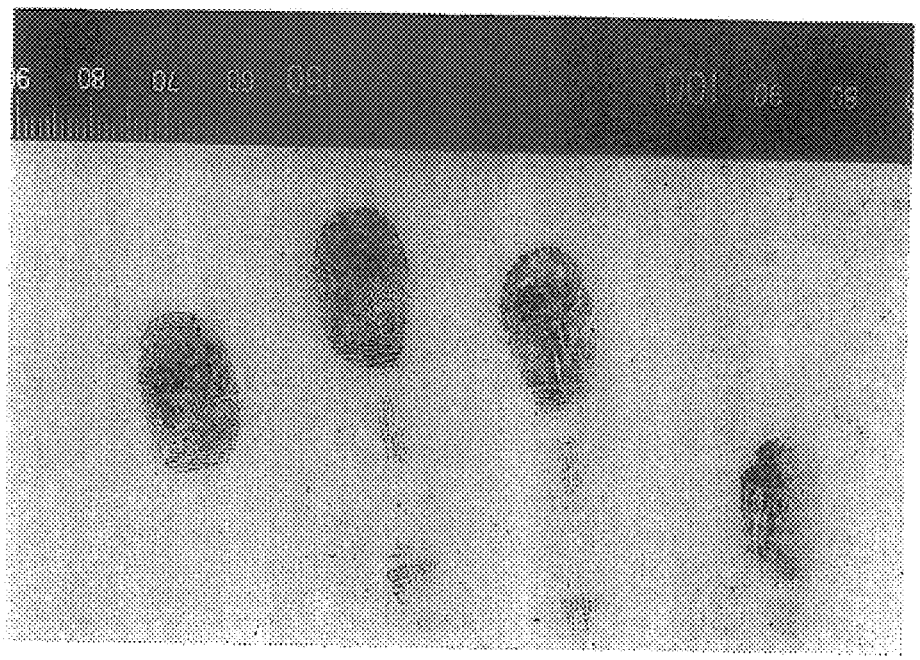
FIG. 10 is a photograph representing the print on gelatin paper for the fingerprint shown in FIG. 9.
Figure 11:
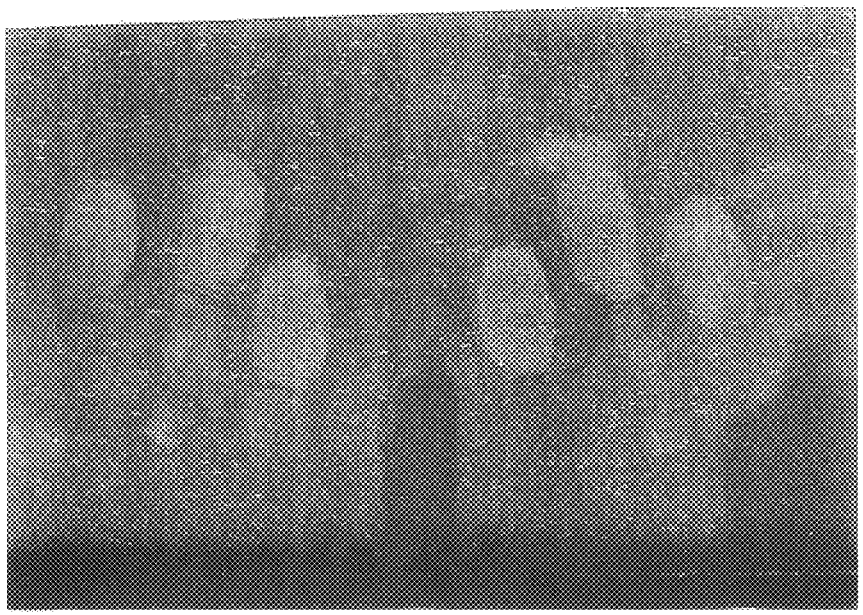
FIG. 11 is a photograph depicting the result of a fingerprint detecting experiment.
Figure 12:
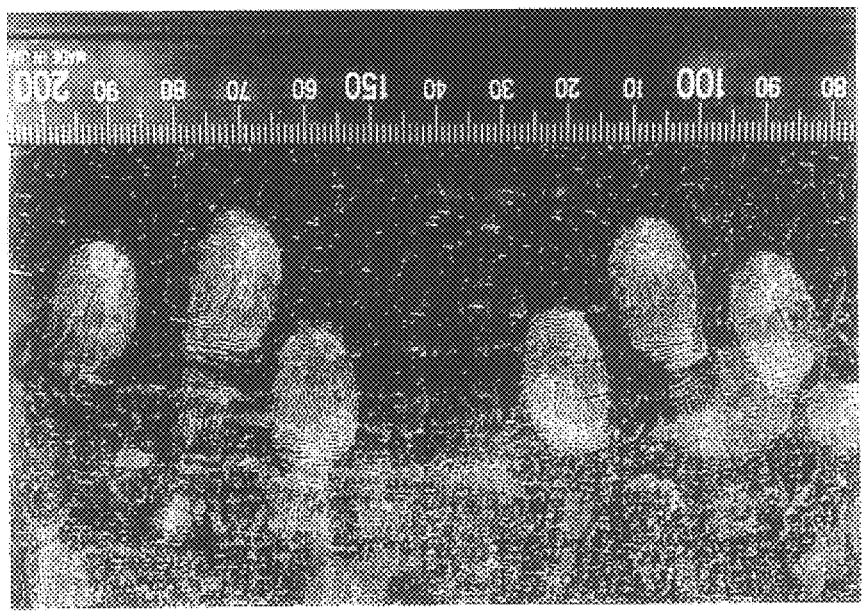
FIG. 12 is a photograph representing the print on gelatin paper for the fingerprint shown in FIG. 11.
Figure 13:
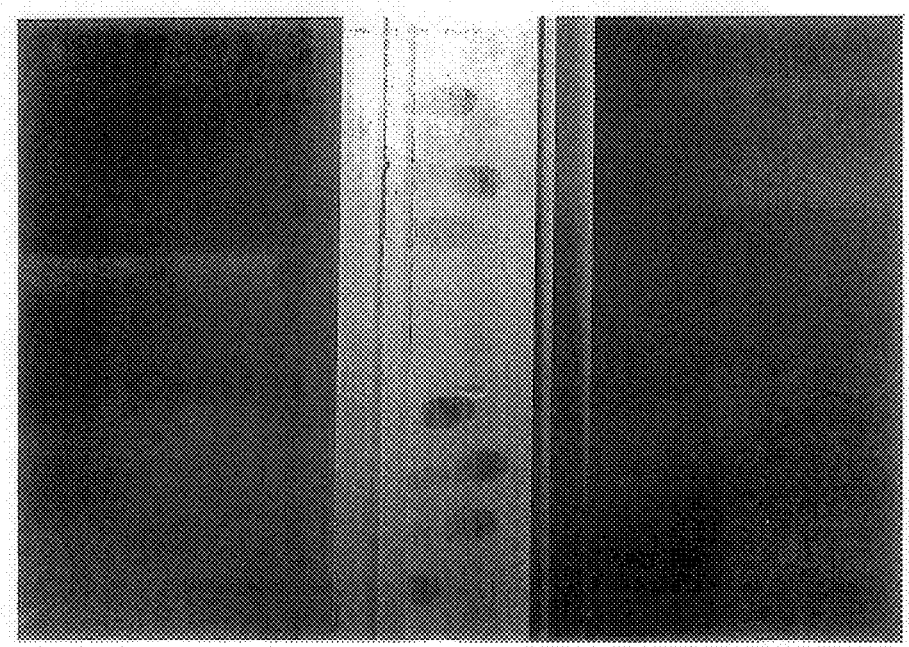
FIG. 13 is a photograph depicting the result of a fingerprint detecting experiment.
Figure 14:
FIG. 14 is a photograph representing the print on gelatin paper for the fingerprint shown in FIG. 13.

FIG. 5 shows an experimental result when the fingerprint detecting agent containing black powder was used to detect the fingerprint which adhered on the window glass of a vehicle: FIG. 6 shows a result of the fingerprint printed on gelatin paper. FIG. 7 shows an experimental result when the white colored fingerprint detecting agent was used to detect a fingerprint adhered on the window glass of a vehicle: FIG. 8 shows a result of the fingerprint printed on gelatin paper. FIG. 9 shows an experimental result when the black colored fingerprint detecting agent was used to detect a fingerprint adhered to a vehicle body: FIG. 10 shows a result of the fingerprint printed on gelatin paper. FIG. 11 shows an experimental result when the white colored fingerprint detecting agent was used to detect a fingerprint adhered on to a vehicle body: FIG. 12 shows a result of the fingerprint printed on gelatin paper. FIG. 13 shows an experimental result when the black colored fingerprint detecting agent was used to detect a fingerprint adhered on a window frame made of aluminum: FIG. 14 shows a result of the fingerprint printed on gelatin paper.

As clear from FIGS. 5 to 14, the fingerprint detecting agent according to the present invention can be applied to detect not only fingerprints adhered on a wet object but also fingerprint on a dried object. Further, even to detect the dried object was investigated, it is possible to investigate a large area speedily by spraying the agent. Therefore, the agent according to the invention has an advantage at this point in comparison to the conventional powder technique.

TABLE 4

| Powder | Glass of Vehicle | Vehicle Body | Aluminum Flame |
|---|---|---|---|
| Black | ◎ | ◎ | ◎ |
| White | ◎ | ◎ | — |

◎: extremely clear
—: not examined (Embodiment 30)

The same operations as those in the Embodiment 9 were taken to obtain a fingerprint detecting agent except that bronze powder (powder of alloy of copper and zinc) was used instead of the zinc oxide. The same fingerprint detecting experiment was carried out as in the same manner tot he above; the obtained result is shown in Table 5.

(Embodiment 31)

The same operations as those in the Embodiment 9 were taken to obtain a fingerprint detecting agent except that copper powder was used instead of the zinc oxide. The same fingerprint detecting experiment was carried out; the obtained result is shown in Table 5.

TABLE 5

| Embodiment | Stabilization of the Soluent (Color of Powder) | Glass | Vehicle Body White | Vehicle Body Black | Aluminum Flame |
|---|---|---|---|---|---|
| 30 | ◎ (Gold) | ◎ | ◎ | ◎ | ◎ |
| 31 | ◎ (Gold) | ◎ | ◎ | ◎ | ◎ |

◎: extremely clear
○: clear
Δ: a little unclear

It can be understood that if gold colored type bronze powder or copper powder is used, the fingerprint can be detected in a good manner without being effected by the basic color of the object to be investigated.

INDUSTRIAL APPLICABILITY

As explained above, according to the invention, the detecting agent is obtained by mixing a special kind of fixer and developer and applied on a latent fingerprint, so that it is possible to detect fingerprint very easily by only spraying the agent, etc, on the latent fingerprint. According to the fingerprint detecting agent and the method for detecting fingerprints of the present invention, even if the object to be detected is in a wet condition, the fingerprint can be detected speedily and accurately.

What is claimed is:

1. A fingerprint detecting agent containing a fixer, a diluent, and a developer: wherein said fixer contains at least one agent selected from a group consisting of silicone series compound, fluoride series compound, hydrocarbon series compound, animal or vegetable oil, higher fatty acid and higher alcohol; wherein said diluent contains polar solvent; wherein said developer contains achromatic colored powder or chromatic colored powder; and wherein said silicone series compound is composed of denaturing silicone and/or dimethyl silicone.

2. A fingerprint detecting agent according to claim 1, wherein said dimethyl silicone has a viscosity of 2 to 1000 cSt.

3. A fingerprint detecting agent according to claim 1, wherein said denaturing silicone is at least one selected from a group consisting of amino denaturing silicone, alkyl denaturing silicone, carboxyl denaturing silicone, polyalkylene denaturing silicone and epoxy denaturing silicone.

4. A fingerprint detecting agent according to claim 1, wherein said fluorine series compound is fluorine oil.

5. A fingerprint detecting agent according to claim 1, wherein said hydrocarbon series compound is at least one selected from a group consisting of liquid paraffin, polybutadiene, and polybutene.

6. A fingerprint detecting agent according to claim 1, wherein said animal or vegetable oil is at least one selected from a group consisting of cottonseed oil, china wood oil and beef tallow.

7. A fingerprint detecting agent according to claim 1, wherein said higher fatty acid is oleic acid and/or stearic acid.

8. A fingerprint detecting agent according to claim 1, wherein said higher alcohol is at least one selected from a group consisting of oleic alcohol, cetanol and synthetic alcohol having a carbon number of 10 to 15.

9. A fingerprint detecting agent according to claim 1, wherein said polar solvent contains water and alcohol group.

10. A fingerprint detecting agent according to claim 9, wherein said alcohol group is a lower alcohol having a carbon number of 1 to 3.

11. A fingerprint detecting agent according to claim 1, wherein a white powder of said achromatic powder contains agalmatolite, lithopone, and zinc oxide.

12. A fingerprint detecting agent according to claim 1, wherein a black powder of said achromatic powder contains carbon black and graphite.

13. A fingerprint detected agent according to claim 1, wherein a gold powder of said chromatic powder is bronze powder and/or copper powder.

14. A fingerprint detecting agent according to claim 1, wherein said achromatic or chromatic powder has a particle diameter of 75 $\mu$m or less.

15. A fingerprint detecting agent according to claim 1, wherein said fingerprint detecting agent contains 0.1 to 5.0 parts by weight of silicone series compound, 85.0 to 98.9 parts by weight of diluent, 1.0 to 10.0 parts by weight of developer.

16. A fingerprint detecting agent according to claim 15, wherein said diluent is composed of 50.0 to 95.0 parts be weight of water, and 5.0 to 50.0 parts by weight of higher alcohol having a carbon number of 1 to 3.

17. A liquid agent for use in manufacturing said fingerprint detecting agent mentioned according to claim 1 being composed of a mixture of said fixer and said diluent.

18. A method for detecting fingerprints using a fingerprint detecting agent according to claim 1, being characterized in that said fingerprint detecting agent is made to contact a latent fingerprint.

19. A method for detecting fingerprints according to claim 18, wherein said latent fingerprint is wet.

20. A method for detecting fingerprints according to claim 18, wherein said contact is carried out by spraying said fingerprint detecting agent on said latent fingerprint or by immersing an object on which said latent fingerprint adheres into said fingerprint detecting agent.

21. A method for detecting fingerprints according to claim 18, wherein an exceeded achromatic or chromatic powder is removed by washing out.

* * * * *

UNITED STATES PATENT AND TRADEMARK OFFICE
CERTIFICATE OF CORRECTION

PATENT NO.    : 6,299,674 B1
DATED         : October 9, 2001
INVENTOR(S)   : Takamura et al.

It is certified that error appears in the above-identified patent and that said Letters Patent is hereby corrected as shown below:

<u>Title page,</u>
Item [30] should read:
-- [30] Foreign Application Priority Data
May 12, 1997   [JP]     9-135,806 --

Signed and Sealed this

Twentieth Day of May, 2003

JAMES E. ROGAN
*Director of the United States Patent and Trademark Office*